United States Patent [19]

Graves

[11] Patent Number: 4,780,314

[45] Date of Patent: Oct. 25, 1988

[54] ISOLATION AND PURIFICATION OF A DIGITALIS-LIKE FACTOR

[75] Inventor: Steven W. Graves, Belmont, Mass.

[73] Assignee: Brigham and Women's Hospital, Boston, Mass.

[21] Appl. No.: 792,918

[22] Filed: Oct. 30, 1985

[51] Int. Cl.$^4$ .................... A61K 35/12; A61K 35/22; A61K 35/14; A61K 35/48

[52] U.S. Cl. ........................ 424/95; 424/199; 424/101; 424/105; 514/27; 514/821; 536/6.1

[58] Field of Search ............... 424/95, 195.1, 99, 100; 514/27, 26; 536/6.1

[56] References Cited

U.S. PATENT DOCUMENTS 4,166,113  8/1979  Norton et al. ................... 514/21
4,339,441  7/1982  Kalmon et al. .................. 514/21

OTHER PUBLICATIONS

Graves, S., et al., Annals of Internal Med., 99: 604-08 (1983).
Devynck, M-A., et al., Brit. Med. J., 287: 631-34 (1983).
Valdes, R., et al., J. of Pediatrics, 102: 947-50 (1983).
Valdes R. et al., J. Clin. Endo. Metab. 60: 1135-43 (1985).
Clarkson, E. et al., Kidney Intl., 16: 710-21 (1979).
Kramer, H., et al., Hormonal Regulation of Sodium Excretion 313-323 (1980).
Cloix, J.-F., et al., Endocrinologie C. R. Acad. Sc. Paris, 296: 213-16 (1983).
Crabos, M. et al., FEBS Letters, 176: 223-28 (1984).
Wainer, I. W. et al., J. Chromatography, 338: 417-21 (1985).
Cloix, J-F., et al., Experientia, 40: 1380-82 (1984).
deThe', H. et al., J. Cardiovas. Pharm., 6: S49-S54 (1984).
Devynck, M.-A., et al., Clin. Exper. Hyper.-Theory and Practice, A6: 441-53 (1984).
Graves, S. W., et al., J. Clin. Endo. Metab., 59: 1070-1074 (1984).
Licht, A., et al., Kidney Intl., 21: 339-344 (1982).
Raghavan, S. R. V. and H. C. Gonick, Proc. Soc. Exp. Bio. Med. 164: 101-104 (1980).
Gonick, et al., J. Clin. Invest., 56: 247-255 (1975).
Chem. Abstrs. 67: 89323m 1967.
Chem. Abstrs. 99: 205491b, 1983.
Chem. Abstrs. 100: 172876d, 1984.
Chem. Abstrs. 101: 65448a, 1984.
Chem. Abstrs. 104: 104976e 1986.
Chem Abstrs. 105: 76916k, 1986.

*Primary Examiner*—John Rollins
*Attorney, Agent, or Firm*—Saidman, Sterne, Kessler & Goldstein

[57] ABSTRACT

This invention relates to a novel recovery process for obtaining the small molecular weight, digitalis-like factor, and further relates to purification of the digitalis-like factor. This invention also relates to the identification and characterization of the factor and to therapeutic uses for the purified factor.

14 Claims, No Drawings

ISOLATION AND PURIFICATION OF A DIGITALIS-LIKE FACTOR

The present invention was made using funds of the United States Government under National Institute of Health grants 1RO1 HL 29950, 1RO1 HL 14944, 1R23 HD 19084-10, and the United States Government has certain rights in this invention.

FIELD OF THE INVENTION

This invention concerns the isolation and purification of a digitalis-like factor from tissue and fluids. This invention also concerns the identification and characterization of the factor.

BACKGROUND OF THE INVENTION

An endogenous factor or family of factors found in animal and human tissue and fluids has been associated with natriuresis, the excretion of abnormal amounts of sodium in the urine. The natriuretic action is believed to result from the inhibition of the Na,K-ATPase enzyme system which mediates active transepithelial sodium transport. Studies have also suggested that this factor may play a pathological role in hypertension. See S. Graves et al., "An Endogenous Digoxin-Like Substance in Patients with Renal Impairment," *Annals of Internal Medicine*, 99: 604–608 (1983); M.-A. Devynck et al., "Measurement of Digitalis-Like Compound in Plasma: Application in Studies of Essential Hypertension," *British Medical Journal*, 287: 631–634 (1983); and R. Valdes et al., "Endogenous Substance in Newborn Infants Causing False Positive Digoxin Measurements," *Journal of Pediatrics*, 102: 947–950 (1983). An association between serum levels of this factor and hypertension in pregnancy has also been found. S. Graves et al., "Endogenous Digoxin—Immunoreactive Substance in Human Pregnancies," *J. Clinical Endocrinol. and Metab.*, 58:748 (1984).

This factor or family of factors cross-reacts with antibodies raised against digoxin, a drug of the cardiac glycoside family. R. Valdes et al., "Protein Binding of Endogenous Digoxin-Immunoactive Factors in Human Serum and Its Variation with Clinical Condition," *J. of Clinical Endocrinol. and Metab.*, 60: 1135–1143 (1985).

As used for purposes of the present invention, this factor is referred to as a digitalis-like factor. It will be understood by those of skill in the art, that other terms may have been used to describe this factor, including digoxin-like and ouabain-like.

Digitalis, digoxin, and ouabain are chemically and pharmacologically related cardiac glycosides, which are used to treat patients with cardiac malfunctions. By increasing the strength of heart muscle contraction, the drugs are indicated in the treatment of congestive heart failure, in atrial flutter and fibrillation, and in paroxysmal atrial tachycardia. There are a significant number of cardiac patients with impaired renal function that are treated with cardiac glycosides. Moreover, patients with renal impairment or renal failure often develop congestive heart failure or malfunctions that are then treated with cardiac glycosides. *Remington's Pharmaceutical Sciences* (16th Ed. 1980) at 654–655, 794–798.

The presence of this digitalis-like factor in serum has a detrimental impact on the measurements of cardiac glycosides by present techniques. Studies have shown that this endogenously produced factor measures as digoxin in the serum of digoxin-free patients with renal impairment. S. Graves et al., "An Endogenous Digoxin-Like Substance in Patients with Renal Impairment," *Annals of Internal Medicine*, 99: 604–608 (1983).

Although the existence of this factor is known, it has yet to be substantially purified and identified. See E. Clarkson et al., "Further Observations on a Low-Molecular-Weight Natriuretic Substance in the Urine of Normal Man," *Kidney International*, 16: 710–721 (1979). The Clarkson study describes a partial purification of the factor from the urine of a normal man, suggesting that the factor may have a molecular weight below 500 daltons; that the natriuretic activity of the factor is relatively resistant to heat at high or low pH, and to oxidation with nitrous acid; that it is insoluble in the less polar organic solvents; and that it is destroyed by prolidase. The factor was separated from the urine using a chromatography column of G-25 Sephadex. The authors suggested that the natriuretic activity is due to a peptide containing the heterocyclic amino acid, proline.

In H. Kramer et al., "Further Studies on Isolation and Purification of a Small Molecular Weight Natriuretic Hormone," *Hormonal Regulation of Sodium Excretion* (1980), 303–323, the authors describe studies on the isolation and partial purification of the factor from human urine. Urine is treated by such steps as gel filtration, high pressure liquid chromatography, reverse phase chromatography, ion exchange chromatography and electrophoresis. At page 320, the authors suggest that the factor may be a small acidic peptide.

J.-F. Cloix et al., "Purification of an Endogenous Inhibitor of Sodium-Potassium-ATPase," *Endocrinologie, C. R. Acad. Sc. Paris*, 296: 213–216 (1983), described the partial purification of the factor from human plasma using gel filtration, followed by anion exchange and high pressure liquid chromatography on reverse phase. M. Crabos et al., "Measurement of Endogenous $Na^+$, $K^+$-ATPase Inhibitors in Human Plasma and Urine Using High-Performance Liquid Chromatography," *FEBS Letters*, 176: 223–228 (1984), used reverse-phase HPLC coupled with Na, K-ATPase inhibition and cross-reaction antibodies to isolate the factor from human plasma and urine. I. W. Wainer, "Rapid Large-Scale Isolation of Biologically Active Molecules Using Reversed-Phase 'Flash' Chromatography: Initial Purification of Endogenous $Na^+$, $K^+$-ATPase Inhibitors from Human Urine," *Journal of Chromatography*, 338: 417–421 (1985), used the method of M. Crabos et al. using "flash" chromatography. J.-F. Cloix et al., "Purification from Human Plasma of Endogenous Sodium Transport Inhibitor(s)," *Experientia*, 40: 1380–1382 (1984), used a purification process for the factor from human plasma comprising (a) inhibition of Na, K-ATPase activity; (b) inhibition of $^3H$-ouabain binding; and (c) cross-reactivity with antidigoxin antibodies. H. de The et al., "Plasma Sodium Pump Inhibitor in Essential Hypertension and Normotensive Subjects with Hypertensive Heredity," *Journal of Cardiovascular Pharmacology*, 6: 549–554 (1984), described isolating the factor from human plasma by Na, K-ATPase activity and by ouabain binding inhibition. M-A. Devynck et al., "Circulating Digitalis-Like Compounds in Essential Hypertension," *Clin. and Exper. Hyper.—Theory and Practice*, A6: 441–453 (1984), isolated a partially purified factor by gel filtration, anion exchange chromatography, and HPLC on reverse phase.

Applicant herein has recognized one of the major problems of isolating and purifying the digitalis-like factor: the vast majority of the factor is protein bound and thus must be separated from its protein binding sites in order to be purified. The seeming failure of the researchers in this area to recognize this problem has limited their success to the partial purification of the factor described above. Indeed, Applicant is the first to isolate and purify the digitalis-like factor to the degree of purity shown in the present invention.

One of the attendant advantages of Applicant's discovery is that it provides for a process which yields sufficient digitalis-like factor (DLF) to permit the factor to be physically and chemically identified. A major difficulty previously encountered in isolating the factor was insufficient quantities of the material. With sufficient yield of the factor, it can be purified and identified. More importantly, once the factor is identified, its potential role as cause or mediator of essential hypertension or pregnancy-induced hypertension can be readily assessed. Such a hypertensionogenic factor has clinical utility and can be used to produce antibodies for passive immunity, to produce immunogenic forms for active immunity, and to produce analogues that can act as antagonists. Any of these uses can then lead to different therapeutic modalities to reduce blood pressure.

The factor, by increasing vascular resistance, also has a therapeutic role in the acute treatment of hypotensive states such as shock. Additionally, because the factor cross-reacts with digoxin antibodies and can inhibit the ouabain-sensitive Na,K-ATPase analogous to digoxin, the factor has utility as an endogenous cardiotropic (ionotropic) agent capable of modifying cardiac function, and can be used as a therapeutic agent in the treatment of congestive heart failure or cardiac arrhythmias, currently treated with cardiac glycosides.

SUMMARY OF THE INVENTION

The invention relates to a novel isolation and substantial purification process for obtaining the endogenous digitalis-like natriuretic factor (DLF).

The invention also relates to the identification and characterization of the factor itself.

The invention further relates to the use of the substantially purified factor.

DETAILED DESCRIPTION OF THE INVENTION

I. ISOLATION AND PURIFICATION PROCESS

In accordance with this invention, the endogenous digitalis-like natriuretic factor (DLF) can be isolated from a sample containing the factor in a simple method for removing the factor from its protein binding sites, allowing for the removal of the factor in a way that is both fast and easily adaptable to treatment of much larger volumes of sample.

Any sample that contains the factor may be used as a starting material according to the method described by this invention. The preferred sample is amniotic fluid, due to its minimal amount of extraneous constituents. However, other samples may be used, including blood plasma, serum, and urine. Tissue that contains the factor includes brain, in particular the hypothalmus, placenta, the adrenals, and the kidneys, and may be used in this invention's method. As used hereinafter, the sample containing the factor will be referred to simply as "sample," which is intended to include any mammalian factor-containing sample.

According to this invention, the digitalis-like factor is removed from factor-containing sample by contacting the sample with a polar solvent under conditions selected to remove the factor from the sample and sample-protein binding sites. The factor, present in the solvent, can then be isolated and subsequently purified. For example, 1.0 ml of serum has no more than 0.01 relative mass units of the factor. However, after the solvent treatment according to this invention, typical amounts of factor recovered from 1.0 ml of serum are close to 3.0 relative mass units, or a 300-fold increase in factor.

More specifically, in the preferred embodiment, the sample is pretreated to isolate the factor-protein complex. Typical pretreatments can include, but are not limited to, lyophilization, heat-treatment by boiling, or protein precipitation by organic solvent.

The isolated factor-containing protein is then contacted and thoroughly dispersed in a polar solvent with a dielectric constant of about 6 or greater. The preferred polar solvents for use in this invention will have a high dielectric constant of about 10 or greater. Dielectric constants of various compounds which may be useful in this invention are given in Gordon and Ford, *The Chemist's Companion* (John Wiley & Sons, 1972) on pages 4–18. For example, polar solvents which may be used in this invention include, but are not limited to, methanol, ethanol, acetone, ethyl acetate, isobutanol, acetic acid, and isopropanol.

The factor is then separated from the serum sample. In the preferred embodiment, centrifugation is used, although it will be understood by those skilled in the art that other means may be used, such as filtration, sedimentation, and the like. Thus, in the preferred embodiment, the solvent and the protein containing the factor are centrifuged; the supernatant from the centrifugation step is decanted and saved, as the factor is now present in the organic phase. In the preferred embodiment, the pellet remaining after decantation of the supernatant is again contacted with the polar solvent to extract any factor still bound to the protein. As will be understood by those skilled in the art, this step may be repeated to increase the yield of the factor from the sample. The factor-solvent supernatant is then treated to remove the solvent and to isolate the factor. Any suitable removal technique may be used, such as evaporation and the like. The residue remaining after removal of the solvent comprises the isolated factor.

This residue, comprising the factor in impure form, may be purified by the use of selective extractions using various solvents, and final purification by a combination of high-pressure liquid chromatography (HPLC) and affinity chromatography. In the preferred embodiment, the factor is purified by the following steps:

(1) The isolated residue, containing the factor, is dispersed with distilled water and extracted with hexane. The aqueous phase, containing the factor, is separated, and taken to dryness in vacuo, leaving a viscous residue solution.

(2) The residue of step (1) is washed successively with methanol. After each wash, the liquid is decanted and filtered through a small, fine filter. The filtrates are then pooled and taken to dryness in vacuo. This step is preferably repeated multiple times to extract the factor from the residue of step (1).

(3) The residue from (2) is brought up in methanol. Ethanol is added and a precipitate forms. The mixture is then centrifuged. After centrifugation, the supernatant containing the factor is decanted and taken to dryness in vacuo.

(4) The residue from (3) is washed with distilled water and the solution centrifuged. The resulting aqueous phase, containing the factor, is ultrafiltered. The ultrafiltrate is taken to dryness in vacuo, then suspended in distilled water.

Final purification is accomplished by applying the ultrafiltrate suspended in distilled water to high pressure liquid chromatography (HPLC) and then to affinity chromatography using antibodies to digoxin bound to protein A-Sepharose 4B.

The HPLC step can be accomplished according to the means known in the art. See, for example, *High Performance Liquid Chromatography for the Biochemist* (LKB 1982). In the preferred embodiment, the ultrafiltrate, suspended in distilled water, is applied to an HPLC column using reverse phase chromatography and the eluate monitored continuously at 225 nm. Using a column eluted with a gradient of $CH_3CN/H_2O$ solution, at a flow rate of 1.0 ml/minute, the fraction elutes at 17-18 minutes elution. This fraction is collected and taken to dryness in vacuo.

The residue of the HPLC fractions at 17, 18 ml elution is brought up in distilled water and applied to an affinity column. The use of affinity chromatography for purification is well known in the art. See, for example, *Affinity Chromatography* (Pharmacia 1973). The affinity column resins employed a primary digoxin antisera (Cambridge Medical Diagnostics, lot #R88223F) covalently coupled to Protein A coupled to Sepharose$^R$ 4B (Sigma Chemical). The activity may be washed from the column using methanol, followed by 0.5M acetic acid, followed by methanol. The methanol and acetic acid washes are pooled and then taken to dryness.

The dried eluate from the affinity chromatography is dissolved in distilled water and then rechromatographed by HPLC using an analytical sized phenylethyl silyl column, eluting at a flow rate of 1.0 ml/minute, with a gradient of $CH_3CN/H_2O$. The fraction elutes at 26-28 minutes elution. This fraction represents the substantially purified digitalis-like factor.

As used herein, the term "substantially pure" or "substantially purified" is meant to describe the factor which is substantially free of any compound normally associated with the factor in its natural state; i.e., free of protein and carbohydrate components. The term is further meant to describe the factor which is homogeneous by one or more purity or homogeneity characteristics used by those of skill in the art. For example, a substantially pure factor will show constant and reproducible characteristics within standard experimental deviations for parameters such as the following: molecular weight, chromatographic techniques and such other parameters. The term, however, is not meant to exclude artificial or synthetic mixtures of the factor with other compounds. The term is also not meant to exclude the presence of minor impurities which do not interfere with the biological activity of the factor, and which may be present, for example, due to incomplete purification.

II. IDENTIFICATION AND CHARACTERIZATION OF THE ENDOGENOUS DIGITALIS-LIKE FACTOR (DLF)

Molecular Weight: The DLF has a low molecular weight. It passes freely through filters having molecular weight cutoffs of 5,000 and 10,000. Using a series of sizing membranes and studying the partition pattern of DLF and dyes of known molecular weight, the estimated molecular weight is from about 150 to about 250 daltons.

Solubility: The DLF is water soluble and is highly polar. The DLF is 100% soluble in 100% methanol, 100% ethanol, and 95% ethanol. Equal volume extractions of aqueous solutions of DLF using methylene chloride or ethyl acetate removed approximately 30% of DLF. Similar extractions using chloroform or hexane removed <5% of the activity.

Stability: Heating DLF in an aqueous solution at 100° C. for 2 hours produced no detectable loss of activity. Heating DLF in 6N HCl for 2 hours produced no detectable reduction in activity. However, extending the incubation period to 24 hours produced a 75% reduction in activity.

Neutrality: The DLF was not bound to strong cation exchange resin between pH 4-8 or to strong anion exchange resin between pH 5-9.

Non-Primary Amine: The DLF incubated with fluorescamine developed no fluorescence and showed no loss of activity.

Non-Peptide: In addition to DLF's small size and apparent absence of primary amine, its activity being unaffected by trypsin and pronase, a non-specific proteolytic enzyme, indicates that the factor is not a peptide.

Not a Fatty Acid or Lipid: The solubility and extraction patterns in conjunction with the finding that the factor is not absorbed or bound specifically to albumin to any appreciable degree, <10%, indicates that the DLF is not a fatty acid, lipid, phospholipid, or other non-polar compound. Additionally, an aqueous DLF solution was extracted with chloroform/methanol ($H_2O:CH_3OH:CHCl_3$; 1:1:2). Using this standard method for lipid or fatty acid removal, less than 30% of the activity was so removed.

Alcohols: The DLF after reaction with benzoylchloride shows a significant loss of activity. Acetyl chloride does not appreciably decrease activity suggesting that either the added bulk of the phenyl ring of benzoylchloride produces steric hindrance or changes DLF solubility sufficiently to decrease activity. In the absence of amines, this indicates an alcohol. Periodate oxidation does not affect activity ruling out vicinal, non-aromatic alcohols, aminoalcohols, or carbonyls, e.g. sugars.

Ketones or Aldehydes: Both bisulfite and sodium borohydride react specifically with aldehydes or ketones. Both agents cause a time related decrease in DLF activity. Bisulfite reacts with only unhindered ketones or aldehydes. DLF contains at least one unhindered ketone or aldehyde.

Catechol: The DLF serves as a substrate or pseudosubstrate for catechol-o-methyl transferase. This enzyme transfers the terminal methyl group from the methionine of (labelled) adenosyl methionine to the DLF. The DLF is recovered as a single peak of radioactivity eluting not at its original 26-28 ml elution, but at 34-36 ml elution using the phenylethylsilyl column and the acetonitrile/$H_2O$ gradient described above (10-30% $CH_3CN$ over the first 20 minutes, 30-90% $CH_3CN$ from 20-50 minutes, and 100% $CH_3CN$ for the last 10 minutes of elution).

In Vitro Activities of Digitalis-Like Factor:

Cross-reactant with Antidigoxin Antibody: The DLF cross-reacts with antidigoxin antibodies utilized in a New England Nuclear digoxin assay. They do not cross-react with some other antidigitoxin antibodies (Beckman) and have decreased cross-reactivity in the Corning Medical digoxin assay.

Inhibitor of Quabain-Sensitive, [Na,K]ATPase: The DLF inhibits a soluble preparation of dog renal quabain-sensitive [Na,K]ATPase.

The DLF also inhibits Rb influx into red blood cells, a reflection also of [Na, K]ATPase inhibition.

III. USE OF THE PURIFIED DIGITALIS-LIKE FACTOR

The substantially purified digitalis-like factor has clinical utility in several areas. As an agonist, this factor may be used in a pharmaceutical composition, comprising an effective amount of the factor with a pharmaceutically acceptable carrier. The factor may be used to treat patients suffering from cardiac malfunctions by administering a therapeutically effective amount of the factor to the patient. In addition, the factor may be used to treat hypotension in a patient suffering therefrom, by administering a therapeutically effective amount of the factor to the patient.

As an antagonist, the factor has utility as a therapeutic agent to produce antibodies for passive immunity for treating hypertension and reducing blood pressure. The factor may also be used to produce immunogenic forms for active immunity against hypertension and high blood pressure. Further, the factor may be used to produce analogues for preparing different modalities to reduce hypertension and blood pressure.

EXAMPLE 1

Extraction and Purification of the Factor

The following example describes the procedure for the isolation and purification of digitalis-like factor (DLF) from amniotic fluid. The choice of amniotic fluid was made to minimize impurities (extraneous constituents of serum) and represents a source that is available in large quantities in which DLF is present in high concentrations. A digoxin radioimmunoassay (New England Nuclear) was used to monitor the purification.

A sample of approximately 100–150 ml amniotic fluid was lyophilized overnight, leaving a dry powdery solid residue.

The residue was washed with 20 ml absolute methanol. The solids were thoroughly dispersed in the methanol (scraping and dividing the material with a spatula) after which the entire mixture was centrifuged (15,000×g, 5° C., 10 minutes). The supernatant was decanted and saved. The pellet was dispersed in 15 ml absolute methanol and centrifuged as before. The supernatant was saved. The pellet was washed another time with 15 ml methanol, and centrifuged as above. The three supernatants, clear, dark yellow in color, were pooled and taken to dryness in vacuo. The pellet was discarded.

The residue, a thick viscous, cloudy yellow liquid was dispersed in 10 ml distilled $H_2O$ and extracted with 10 ml hexane. The organic phase was removed and discarded and the aqueous phase, containing activity, was taken to dryness in vacuo. Under reduced pressure, the aqueous phase had a tendency to splatter during drying.

The residue, a cloudy viscous, brownish-yellow solution was washed thoroughly with 4.0 ml absolute methanol. The liquid was removed in a way to minimize the amount of solids transferred and was filtered through a small, fine filter. The solids in the vessel were washed two more times with 2.0 ml methanol, the liquid removed, filtered, and the three washes pooled and taken to dryness in vacuo.

The residue was crystalline to oily, yellowish-brown, and cloudy. It was washed successively with 2.0, 1.0 and 0.5 ml methanol. After each wash, the liquid was removed and filtered. The washes were pooled and taken to dryness in vacuo.

The residue, a yellowish oil, was brought up in 1.0 ml methanol and 95% ethanol was added until no further precipitation was detectable (10–15 ml). The ethanol produced an off-white flocculent precipitate. The mixture was centrifuged at 2,500×g, 4° C., for 10 minutes. The liquid was removed and taken to dryness in vacuo. The pellet was discarded.

The residue was suspended in 1.0 ml distilled $H_2O$, washed with an additional 0.5 ml $H_2O$ and the solution ultracentrifuged at 95,000×g, 4° C., for 45 minutes. A brownish-green material was layered on top of the aqueous phase. The aqueous phase was carefully removed and the brownish-green material discarded.

The ultrafiltrate was taken to dryness in vacuo and suspended in 0.3–0.5 ml distilled $H_2O$. This was applied to a high performance liquid chromatography column ($C_{18}$-reversed phase column, 30 cm, Waters Bondapak). The column was eluted at room temperature using an acetonitrile/$H_2O$ gradient with a flow rate of 1.0 ml/min. The column had been washed and equilibrated with 20% $CH_3CN$/80% $H_2O$, a linear increase from 20% $CH_3CN$ to 100% $CH_3CN$ over the next 20 minutes and then an additional 10 minutes elution at 100% $CH_3CN$. The eluate was monitored continuously at 225 nm using UV spectrophotometry. The fraction of interest eluted at 17–18 ml elution. This fraction was collected and taken to dryness in vacuo.

The residue (nothing visible) of the HPLC fractions at 17, 18 ml elution was brought up in 1–3 ml $H_2O$ and applied to a 1.0 ml affinity column. The column resins employed a primary digoxin antisera (Cambridge Medical Diagnostics, lot #R88223F) covalently coupled to Protein A coupled to Sepharose 4B (Sigma Chemical). The process for covalently bonding the antisera to Protein A followed closely the procedure of Schneider, *J. Biol. Chem.*, 250: 10766 (1980). The column was tumbled with solution containing activity at room temperature for 16 hours. The column was allowed to drain, washed with 5.0 ml 1.0M ammonium acetate followed by 10.0 ml of distilled $H_2O$. The activity was eluted from the column with 5.0 ml absolute methanol, followed by 5.0 ml 0.5M acetic acid, followed by 5.0 ml of methanol. The methanol and acetic acid solutions were pooled and taken to dryness in vacuo. All the acetic acid was removed.

The eluate was dissolved in 0.4 ml–0.5 ml of very pure $H_2O$ and rechromatographed by HPLC using an analytical sized phenylethyl silyl column (Corning, Zorbax Phenyl, 4.6 mmID×25 cm) eluted at a flow rate of 1.0 ml/min with a gradient of $CH_3CN$/$H_2O$. The gradient began at 10% $CH_3$90% $H_2O$ (the column having been well washed and equilibrated). The gradient increased to 30% $CH_3CN$/70% $H_2O$ over the first 20 minutes of elution. Then the $CH_3CN$ was increased to 90% $CH_3CN$ (the balance $H_2O$) between 20 and 50 minutes of elution and finally the $CH_3CN$ was jumped to 100% for the last 10 minutes of elution. Again, the eluate was monitored concurrent with elution by UV spectrophotometry at 225 nm, 0.02 absorbance units full scale. Elution of a single peak of activity (as monitored by digoxin RIA) was identified at 26–28 minutes elution. There was no absorbance in the UV for this fraction. This fraction represents highly purified digitalis-like factor.

EXAMPLE 2

Physical and Chemical Characteristics of the Factor

The following example describes the procedures used to determine the physical and chemical properties of the factor.

Molecular Weight: An ultrafiltration apparatus (Amicon) was used with YM-10 and YM-5 filtration membranes having nominal molecular weight and cutoffs of 10,000 and 5,000 daltons. Filtrations were carried out at 4° C., under 70 p.s.i. $N_2$ gas, with constant stirring. Filters had been previously washed with 3 ml each of 95% ethanol and $H_2O$. Gel filtration experiments were performed using a 175 ml (2.5×35 cm) column G-25 Sephadex which had been previously swollen in 10 mM ammonium acetate, pH 6.8. To this column was applied the DLF containing solution (less than or equal to about 2 ml, not protein bound), and eluted with the same buffer at 4° C. at a rate of 100 ml/hr elution. A NOVA 1 analyzer was used to measure Na and K concentration in the various 2.0 ml factors. Sizing studies followed the method described in the paper by Valdes and Graves, *J. Clinical Endocrinol. and Metab.*, 60: 1135–1143 (1985), using a 3.0 ml Amicon ultrafiltration cell and filtration membranes with molecular weight cutoffs from 500–10,000.

Solubility: Concentrations of DLF representing >100-fold more than is routinely measured in normal human serum and >10-fold more than is routinely measured in human amniotic fluid were solubilized in $H_2O$, methanol, ethanol or 95% ethanol, transferred quantitatively, the solvent removed and the DLF reconstituted in $H_2O$ and analyzed by RIA. Extractions involved DLF in 5 ml $H_2O$ being shaken with 5 ml of various non-water miscible organic solvents, the two phases separated, taken to dryness in vacuo and reconstituted in $H_2O$ at the initial volume and assayed by RIA.

Stability: The DLF was heated (1) in an aqueous solution at 100° C. for 2 hours and (2) in 6N HCl at 100° C. for 2 hours. The acid hydrolysis employed a lyophilization step to remove the HCl prior to reconstitution in $H_2O$ and assay by RIA.

Neutrality: The procedure used is outlined in Valdes and Graves, *J. Clinical Endocrinol. and Metab.*, 60: 1134–1143 (1985), and is a slight modification of the method outlined in *Ion Exchange Chromatography*, Pharmacia Fine Chemicals AB, Uppsala, Sweden.

Non-Primary Amines: Aliquots (100 ul) of HPLC fractions with and without DLF activity were added to 1.4 ml 0.2M borate buffer (pH 9.0). While mixing vigorously, 0.5 ml of fluorescamine (30 mg/100 ml acetone) was added. Fluorescence was sought using an excitation wavelength of 390 nm while scanning for emissions between 425 and 525 nm. The solutions were taken to dryness and reconstituted in 0.5 ml $H_2O$, the pH adjusted to pH 7.4 and 100 ul aliquoted for RIA. A second 100 ul portion of the HPLC fraction containing DLF activity was diluted with 0.2M borate buffer 1.5 ml and 0.5 ml acetone added. The solution was dried and reconstituted in 0.5 ml $H_2O$, the pH adjusted to 7.4. This served as a control. No loss of activity was detected by RIA after treatment with fluorescamine. Fluorescamine by itself had no appreciable effect on the assay.

Non-peptide: Two aliquots of HPLC fraction containing DLF activity were added to a buffer solution (10 mM $NaHPO_4$, pH 7.4) for 30 minutes with and without pronase (1 mg protein or 15 units enzyme activity). If peptide were present, it should turnover substrate at a rate of 15 umol/min. or 20.5 mmol/incubation. No difference was seen in the activity of the treated and untreated DLF. Trypsin with equivalent specific activity and in equivalent amounts produced no effect either.

Not a Fatty Acid or Lipid: Solubility and extraction studies are described above. Bovine or human serum albumin (10 ul of 10% solution) added to 100 ul of DLF solution showed <10% decrease in activity. A 100 ul aliquot was diluted to 1.0 ml $H_2O$ and then extracted with chloroform-methanol ($H_2O$, $CH_3OH$, $CHCl_3$, 1:1:3), carried out as other extractions were.

Alcohols: The experiments using acetyl chloride were as follows: To a tube were added 50 ul DLF solution and the DLF solution was taken to dryness in vacuo. To this, 20 ul acetyl chloride was added and the tube capped and allowed to sit for 1 hour. The excess acetyl chloride was destroyed by addition of 500 ul $H_2O$. The solution was taken to dryness, removing the acetyl chloride, acetic acid and HCl. Water (100 ul) was added to reconstitute. To a second tube was added 20 ul acetyl chloride followed by addition of 500 ul $H_2O$. To this solution was added 50 ul of the same solution and the solution was taken to dryness and reconstituted in 100 ul $H_2O$. To this solution was added 20 ul acetyl chloride followed by 100 ul $H_2O$. The first tube represents exposure of DLF to active reagent. The third tube is a negative control. The second is a DLF containing control. Tubes 1 and 2 showed comparable activity suggesting that either no hydroxyls or amines (shown in other experiments described herein not to be present) were present or that modification did not decrease activity. Studies with benzoyl chloride were carried out as follows: To the first tube was added 50 ul DLF solution, 20 ul benzoyl chloride and 10 ul pyridine which were allowed to incubate one hour. Then 0.5 ml of $H_2O$ was added and this solution extracted with 2.0 ml hexane. The hexane was removed. The aqueous phase was taken to dryness in vacuo and reconstituted in 100 ul $H_2O$. To a second tube was added 20 ul benzoyl chloride, 10 ul pyridine and 450 $H_2O$. After one hour 50 ul DLF solution was added and the solution was extracted with 2.0 ml hexane with work up as stated. In tube three, 20 ul benzoyl chloride, 10 ul pyridine and 500 ul $H_2O$ were mixed. After an hour, the solution was extracted with 2.0 ml hexane with workup as described. Tube three should read near zero. Decreased activity was seen for tube one consistent with benzoylation of DLF and decreased activity due to steric crowding or less polarity or both. This is compatible with a hydroxyl group. Additionally, the acetyl chloride treated DLF was rechromatographed on HPLC under equivalent conditions and the activity eluted at later retention times, again strongly suggesting that hydroxyl groups are present and are modified by acetylation. In other experiments, an aliquot of DLF was taken to dryness in vacuo. To this was added 50 ul 2% sodium periodate solution. After incubation for 30 minutes at 50° C., the excess periodate was stopped with 50 ul 10% sodium bisulfite. To a second tube was added first the 50 ul periodate and 50 ul bisulfite followed by the DLF. No difference was seen between the two tubes consistent with the compound not containing non-aromatic vicinal diols as would be found in sugars.

Ketones or Aldehydes: The previous experiment did show that DLF activity was sensitive to bisulfite independent of periodate. Experiments with bisulfite were as follows. A 25 ul aliquot of DLF solution was mixed with 25 ul H$_2$O and 50 ul 10% bisulfite or 75 ul H$_2$O. The bisulfite had negligible effect on the assay by itself: the bisulfite-free DLF tube after an hour had a value of 1.62 units activity. Incubation with bisulfite for 30 minutes reduced activity to 0.72 units, and 60 minutes incubation reduced the activity to 0.55 units. Bisulfite is selective for aldehydes and/or unhindered ketones. To confirm their presence, experiments were conducted with sodium borohydride, a reducing agent quite selective for aldehydes and ketones. A 40 ul aliquot of DLF was added to 200 ul H$_2$O and 1 mg sodium borohydride. After 2 hours at 50° C., the reaction was stopped with 5 ul concentrated acetic acid. A second tube (control) contained 240 ul H$_2$O, 1 mg sodium borohydride and 5 ul concentrated acetic acid, followed by addition of 40 ul DLF solution. The activity of DLF was reduced from 0.9 units to 0.5 units by exposure to borohydride.

Catechol: The method used to assess the presence of a catechol follows the method used for catecholamines. It is a radioenzymatic assay that represents a modification of the method of Peuler and Johnson, "Simultaneous Single Isotope Radioenzymatic Assay of Plasma Norepinephrine, Epinephrine, and Dopamine," *Life Sciences*, 21: 625 (1977). Methyl-labelled $^3$H-Sadenosyl methionine ($^3$H-SAM) is used to 3-0$_3$-methylate the catecholamines in 50 ul plasma, 50 ul urine; the resulting products being H$^3$-normetanephrine, H$_3$-metanephrine, and H$^3$-3-methoxytyramine. These are separated by thin layer chromatography and a periodate reaction.

Catechol-O-methyl transferase, COMT, is used to catalyze the reaction and is prepared from rat livers according to the method of Cuello, Hiley and Iversen. Benzylhydroxylamine hydrochloride is used to inhibit the formation of dopamine from plasma DOPA due to the DOPA decarboxylase activity present in the COMT preparation. EGTA is added directly to the plasma sample to prevent the inhibitory influence of plasma calcium.

Na,K-ATPase Assay: The method is described in the paper by Graves and Williams, *J. Clin. Endo. Metab.*, 59: 1070–1074 (1984).

Digoxin Radioimmunoassay: The method follows that described in the paper by Graves and Williams, ibid.

$^{86}$Rd Red Blood Cell Assay: This assay was performed by the following procedure: Human red cells were loaded by the nystatin procedure to contain saturating amounts of Na (75 mM Na+75 mM K). Subsequently, Rb influx was measured from a media containing 140 mM Na and 2 mM K in the absence of ouabain, and in the presence of graded amounts of ouabain ($10^{-9}$ to $10^{-4}$M). A titration curve of Rb influx was obtained as a function of ouabain concentration. To test the inhibitory activity of plasma or tissue extracts and fractions separated by HPLC or other purification procedures, the Na-loaded red cells are pre-incubated in the influx media (without isotope) for 1 hour; afterwards, $^{86}$Rb is added and triplicate samples are removed at 30 minutes for influx measurements. This assay can detect levels of inhibition corresponding to concentrations of ouabain in the $10^{-9}$ to $10^{-6}$M range with precision; under the conditions of this assay, the Rb influx is independent of intracellular Na because the Na pump is saturated.

Although the instant disclosure sets forth all essential information in connection with the invention, the numerous publications cited herein may be of assistance in understanding the background of the invention and the state of the art. Accordingly, all of the publications cited are hereby incorporated by reference into the patent disclosure. Moreover, although the foregoing invention has been described in some detail by way of illustration and example for purposes of clarity of understanding, it will be obvious that certain changes and modifications may be practiced within the scope of the invention, as limited only by the scope of the appended claims.

What is claimed is:

1. A substantially purified digitalis-like factor having natriuretic activity wherein said factor:
   (i) has a molecular weight of about 150–250 daltons;
   (ii) is highly polar;
   (iii) is non-proteinaceous;
   (iv) loses activity when exposed to benzoylchloride;
   (v) reacts with bisulfite and sodium borohydride;
   (vi) acts as a substrate or pseudo-substrate for catechol-O-methyl-transferase; and
   (vii) inhibits Rb influx into red blood cells.

2. A pharmaceutical composition useful for treating patients with cardiac malfunctions comprising an amount of the factor of claim 1 effective to treat said cardiac malfunctions and a pharmaceutically acceptable carrier.

3. A method of treating cardiac malfunction in a patient suffering therefrom by administering a therapeutically effective amount of the factor of claim 1 to said patient.

4. A method for recovering a digitalis-like factor from a mammalian sample containing a digitalis-like factor comprising:
   (a) contacting said mammalian sample containing a digitalis-like factor with a polar organic solvent having a dielectric constant of at least about 6 to isolate said factor from said sample;
   (b) separating said factor from said sample by separation means that maintain said factor in said solvent; and
   (c) recovering said digitalis-like factor from said solvent by means to remove said solvent from said factor.

5. The process of claim 4 wherein said recovery of said digitalis-like factor is accomplished by evaporating said solvent to form a residue containing said digitalis-like factor.

6. The method of claim 5 further comprising purifying said digitalis-like factor.

7. A digitalis-like factor obtainable by a process comprising:
   (a) separating a digitalis-like factor from a sample containing said factor by contacting said sample with a polar organic solvent selected from the group consisting of methanol, ethanol, acetone, ethyl acetate, isobutanol, acetic acid, and isopropanol, having a dielectric constant of at least 6, and separating said factor from said sample by separation means that maintain said factor in said solvent;
   (b) recovering said factor from said solvent by means to remove said solvent from said factor; and
   (c) purifying said factor by selective extraction means and chromatographic means.

8. The method of claim 4 wherein said polar organic solvent is selected from the group of solvents consisting of methanol, ethanol, acetone, ethyl acetate, isobutanol, acetic acid, and isopropanol.

9. The method of claim 8 wherein said polar organic solvent is methanol.

10. The method of claim 4 wherein said sample is selected from the group consisting of serum, blood, tissue, urine, and amniotic fluid.

11. The method of claim 4 wherein said sample is lyophilized prior to contacting with said solvent to form a precipitate and wherein said precipitate is recovered and then contacted with said solvent.

12. The method of claim 4 wherein said sample is heat-treated prior to contacting with said solvent to form a precipitate and wherein said precipitate is recovered and then contacted with said solvent.

13. The method of claim 4 wherein said factor is separated from said sample by centrifugation, filtration, or sedimentation.

14. The method of claim 4 wherein said factor is recovered from said solvent by removing said solvent by evaporation.

* * * * *